United States Patent [19]

Nanji

[11] Patent Number: 4,988,628

[45] Date of Patent: Jan. 29, 1991

[54] METHOD OF DRUG DETECTION

[75] Inventor: Amin A. Nanji, Wellesley, Mass.

[73] Assignee: New England Deaconess Hospital Corporation, Boston, Mass.

[21] Appl. No.: 316,650

[22] Filed: Feb. 28, 1989

[51] Int. Cl.$^5$ ............... G01D 30/00; G01D 33/94
[52] U.S. Cl. ................ 436/173; 250/282; 250/287; 436/175; 436/178; 436/181; 436/901
[58] Field of Search ............. 250/288, 288 A, 287, 250/282; 436/161, 901, 173, 92, 98, 93, 96, 175, 177, 178, 181

[56] References Cited

U.S. PATENT DOCUMENTS

| | | | |
|---|---|---|---|
| 4,194,884 | 3/1980 | Rounbehler et al. | 23/232 R |
| 4,468,468 | 8/1984 | Benninghoven et al. | 436/178 |
| 4,472,631 | 9/1984 | Enke et al. | 250/288 |
| 4,633,083 | 12/1986 | Knorr et al. | 250/287 |
| 4,698,071 | 10/1987 | Elias | 55/390 |
| 4,732,046 | 5/1988 | Lawrence et al. | 73/864.21 |
| 4,754,135 | 6/1988 | Jackson | 250/287 |
| 4,769,540 | 9/1988 | Mitsui et al. | 250/288 |
| 4,774,408 | 9/1988 | Gohlke | 250/287 |
| 4,777,363 | 10/1988 | Eiceman et al. | 250/287 |
| 4,778,993 | 10/1988 | Waugh | 250/288 |
| 4,797,554 | 1/1989 | Blanchard et al. | 250/287 |

FOREIGN PATENT DOCUMENTS 1201646 3/1986 Canada .

OTHER PUBLICATIONS

Huber, J. F., Matisova, E., Kenndler, E., "Effects of Column Parameters on Optimization of Gas Chromatography/Mass Spectrometry" Anal. Chem., 1982, vol. 54, pp. 1297–1304.
Brunnee, C., "Deflection of Charged Particles in Magnetic Fields," Spectra, vol. 9, Nos. 2 and 3, 1983, pub. Finnigan MAT.
Settlage, J.; Jaeger, H.; "Advantages of Fused Silica Capillary Gas Chrometography for GC/MS Applications", J. of Chromatographic Science, vol. 22, May 1984, pp. 192–197.
Lawrence, A. H.; "Characterization of Benzodiazepine Drugs by Ion Mobility Spectrometry", Anal. Chem. 1989, vol. 61 (4), Feb. 15, 1989, pp. 343–348.
Jolley et al. (1981) Clin. Chem. 27/9:1575–1579.
Lawrence (1986) Analytical Chemistry, 58 No. 6:1069–1272.
Caplan et al. (1987) Clin. Chem. 33/7:1200–1202.
Lawrence (1987) Forensic Science International, 34:73–83.
Nanji et al. (1987) Clinical Toxicology 25(6):501–515.
Nanji et al., (1988)International Journal of Clinical Pharmacology, Therapy and Toxicology, 26 No. 1:1–3.

Primary Examiner—Robert J. Hill, Jr.
Attorney, Agent, or Firm—Lahive & Cockfield

[57] ABSTRACT

Disclosed are methods of rapidly and accurately detecting a compound-of interest, such as a toxic drug, in a body fluid. A liquid sample containing various native constituents and an anticipated exogenous chemical compound is obtained from the body. The sample is then subjected to analysis by ion mobility spectrometry to determine the presence of the exogenous chemical compound or related metabolite therein. The method may further include the step of separating the compound-of-interest from said native constituents in said fluid sample prior to analysis.

8 Claims, 1 Drawing Sheet

METHOD OF DRUG DETECTION

BACKGROUND OF THE INVENTION

The present invention relates to methods of detecting chemical compounds in liquids, and more particularly, to drug screening methods which are rapid, highly specific, and which can be performed on extremely small body fluid samples non-invasively or invasively obtained.

Prompt and accurate toxicologic laboratory information is important in the treatment of patients admitted to the hospital with drug overdose. Because the type of drugs involved in drug abuse are not often known, it is necessary to have both screening methods and definitive methods for identification, both of which must be able to be performed rapidly so that proper treatment can be administered as quickly as possible. In addition, a positive or negative finding eliminates the need for further extensive diagnostic work up.

A number of factors must be considered in selecting the type of screening and analytical methods for routine drug screening, and for and processing large numbers of samples. These factors include sensitivity, specificity, reproducibility, speed, simplicity, and cost. In addition, both the phase of the sample (i.e., solid, liquid, gas), and the ease of obtaining that particular sample must also be taken under consideration when selecting a detection method. Procedures currently available for drug detection in various body samples include thin layer chromatography, gas chromatography, high pressure liquid chromatography, various immunoassays, and gas chromatography-mass spectrometry.

Thin layer chromatography (TLC) has traditionally been used as a broad spectrum screen for drugs of abuse. This procedure is relatively inexpensive and does not require sophisticated instrumentation. However, TLC is insensitive; it yields qualitative (i.e., positive or negative) results only. Typically the minimum amount of drug or metabolite required to yield a positive result is in the 1-2 mg/ml range. Therefore, negative results may imply that the sensitivity of the method is inadequate for detection of drugs in the sample. Thus, the TLC screen is only useful for emergency room purposes where quick determination of a toxic level is necessary, and would not be used to detect low level substance abuse. Another problem with TLC is the relative lack of specificity. Under ideal conditions, a specific drug will always migrate to the same spot on TLC plates; however, similar molecules and other drugs may travel in approximately the same zone. Furthermore, TLC is labor intensive and may result in highly variable results between laboratories or even for a particular given laboratory.

Gas chromatography (GC) is an analytical technique that separates molecules by means of glass or metal tubing coated or filled, respectively, with material of particular polarity. The sample is vaporized at the injection port and carried through the column to the detector by a steady flow of gas. Separation of the compounds, and hence their detection is dependent on their interaction with the column packing. This detection method is limited because only gases and liquids with fairly low boiling points (e.g., methanol and ethanol) can be analyzed; most drugs of abuse have higher boiling points, and therefore, cannot be detected.

Gas chromatography-mass spectroscopy (GC-MS) is a method commonly used for confirmation of a positive analysis obtained by another screening method. GC-MS analyzes a liquid or gaseous substance according to its fragmentation pattern; the exact mass of the fragments is compared to a computer library resulting in a "fingerprinting" of molecules. The procedure is very costly and requires a high degree of technical expertise for its operation.

High pressure liquid chromatography (HPLC) is similar to GC with the exception that liquids rather than gas are used to propel substances through the columns. Unfortunately, this procedure is also time consuming and requires a high degree of technical expertise for its operation.

Immunoassays operate on the principle of antigen-antibody interactions, and may include the use of enzyme, fluorescent, or radioactive labels. Liquid samples can be easily analyzed. One widely used immunoassay for detecting toxic substances is the enzyme multiplied immunoassay (EMIT) system which works on the basis of an inhibition of an enzyme substrate reaction proportional to the amount of drug present in the sample (usually urine). Another useful analytical method is the fluorescence polarization immunoassay (FPIA) which has been applied to drug abuse testing in urine. (See, e.g., Jolley et al. (1981) Clin. Chem. 27:1575-1579; and Caplan et al. (1987) Clin. Chem. 33:1200-1202).

The reliability of any immunoassay depends on the specificity or sensitivity of the antibodies. Thus, the presence of compounds which cross-react with the antibody can result in a false negative or false positive result. In addition, a drug assay that is reported as negative may actually contain small amounts of drug diluted in a large volume of liquid sample. Other factors may also alter this sensitivity such as the pH and age of the sample, and the presence of contaminating substances (e.g., vinegar, soap) therein. Another disadvantage of immunoassay is the lack of specificity. Antibodies to drug antigens are notoriously non-specific and commonly used over the counter medications such as phenylisopropyl-amines, ephedrine, and phenylpropalamine react with antibodies in clinically obtained concentrations.

Ion mobility spectrometry is an analytical method that has been used to analyze gaseous samples, for example, in ambient atmospheres (Canadian Patent No. 1201646) and drug particles in contact with the skin surface (Nanji et al. (1987) Clin. Toxicol. 25:501-515). This technique distinguishes ionic species on the basis of the difference in the drift velocity of ions through gas under an applied electric field.

There is however, no known method of screening liquid samples of body fluids for a wide range of toxic compounds which is rapid, sensitive, accurate, and easy to perform.

Accordingly, it is an object of the present invention to provide a rapid, yet sensitive and specific method of drug screening.

It is another object of the invention to provide a method of detecting a wide range of toxic drugs in a liquid sample of a body fluid.

Another object to provide a method of detecting a plurality of chemical compounds in a body fluid sample.

Yet another object is to provide a non-invasive method of detecting a chemical compound in a body fluid.

Still another object is to provide a rapid method of detecting a chemical compound in a small volume of a body fluid.

SUMMARY OF THE INVENTION

The present invention is directed to methods of rapidly and accurately detecting a chemical compound, such as a toxic drug, in a body fluid. It has been discovered that ion mobility spectrometry, a known method of analyzing gaseous samples, can be used for the accurate and sensitive analysis of liquid samples as well. This method has the ability to screen for a wide range of common drugs of abuse, and can be used to identify a plurality of drugs per sample. In addition, it can be performed on extremely small volumes of invasively or non-invasively obtained liquid body samples.

Briefly, a liquid sample containing various native constituents and an anticipated exogenous chemical compound is obtained from the body. The sample is then subjected to analysis by ion mobility spectrometry to determine the presence of the exogenous chemical compound or related metabolite therein.

Exogenous chemical compounds include any number of toxic drugs and drugs subject to abuse which have been put into the body, and their metabolites or breakdown products, hereinafter referred to as "compounds-of-interest". Such compounds include, for example, benzodiazepines (e.g., flurazepam, diazapam, and oxazepam), cocaine, lorazepam, heroine, amytryptyline, and chlorpromazine (also see TABLE 2 set forth below). Evidence of the introduction of these compounds into the body can be found in various body fluids from which samples can be obtained for analysis. Native constituents include various polypeptides, glycoproteins, fatty acids, proteolipids, water, and other components normally making up a body fluid.

In preferred embodiments of the invention, the compound-of-interest is separated from the fluid constituents prior to its analysis. Separation may be accomplished by adsorbing the liquid sample onto an adsorbent, and then removing or desorbing the native constituents therefrom, leaving the compound-of-interest still adsorbed thereto. The compound-of-interest may then be desorbed from the adsorbent and analyzed by ion mobility spectrometry.

A preferred method of achieving separation involves converting the native constituents to a vapor phase, for example, by heating the adsorbent to a first temperature sufficient to vaporize them. The vaporized native constituents are then vented away from the adsorbent. The adsorbed compound-of-interest may then be desorbed from the adsorbent by heating it to a second temperature that is higher than the first temperature, thereby converting it to the vapor state. It is then vented into the ion mobility spectrometer by an inert carrier gas such as nitrogen.

An alternative separation method includes venting the vaporized compound-of-interest to a second adsorbent having an affinity therefor. The adsorbed compound-of-interest may then be desorbed from the second adsorbent by converting it to the vaporized phase. Again, this may be accomplished by heating the second adsorbent to a third temperature sufficient to vaporize said compound-of-interest. The vaporized compound-of-interest is then vented to an ion mobility spectrometer (IMS) for analysis.

BRIEF DESCRIPTION OF THE DRAWINGS

The foregoing and other objects of this invention, the various features thereof, as well as the invention itself, may be more fully understood from the following description, when read together with the accompanying drawings in which.

DESCRIPTION OF THE INVENTION

The detection method of the present invention involves obtaining a liquid sample of a body fluid from a subject, and analyzing it by ion mobility spectrometry. Ion mobility spectrometry has typically been used to analyzed gaseous samples (see, e.g., Canadian Patent No. 1201646). However, it has been discovered that small quantities of liquid samples containing a number of toxic compounds can be accurately and easily analyzed as well.

Evidence of toxic compound abuse can be found in various body fluids from which samples can be obtained for analysis. Useful fluids include invasively obtained fluids, such as blood, serum, amniotic fluid, and cerebrospinal fluid, and non-invasively obtained fluids, such as saliva, semen, urine, and lacrimal gland secretions, the latter group of fluids being particularly useful in cases where the patient is unwilling or unable to give invasively obtained samples. The sample is then subjected to ion mobility spectrometry.

In the preferred embodiment, the native constituents of the sample are separated from the compound-of-interest before ion mobility spectrometry is performed. Any number of separation methods known to those skilled in the art may be employed such as, for example, various types of chromatography or differential centrifugation. One separation method includes the use of an adsorbent capable of retaining the fluid sample, and then of releasing or desorbing the native constituents at temperatures lower than that at which the compound-of-interest is desorbed.

Another separation method includes the use of a sampler-concentrator. Briefly, the device contains two different fluid sample adsorbents and differentially desorbs fluid constituents in two stages. The fluid sample is adsorbed to a first adsorbent having an affinity for the fluid sample, which upon heating to a first temperature, desorbs the native constituents in vapor phase therefrom. The released native constituents are vented away from the device. Upon heating to a second (higher) temperature, the first adsorbent then desorbs the compound-of-interest (and most anything else still adsorbed thereto) in vapor phase to a second adsorbent. The compound-of-interest is delivered to, and preferentially adsorbed and retained by, the second adsorbent, which, upon heating to a third temperature, releases the compound-of-interest in vapor form. The vaporized compound-of-interest is then analyzed by the IMS.

Figure 1:
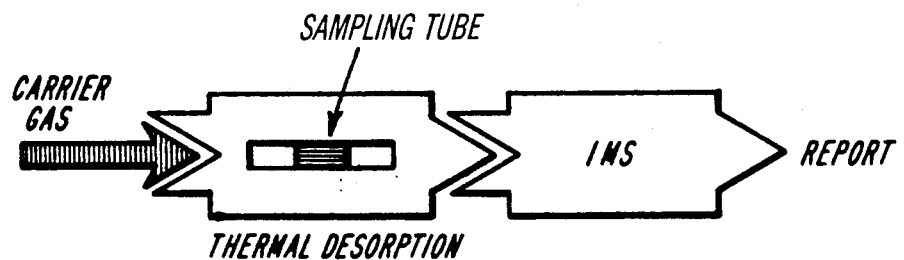
FIG. 1 is a schematic representation of a preferred embodiment of the present invention.
Figure 2:
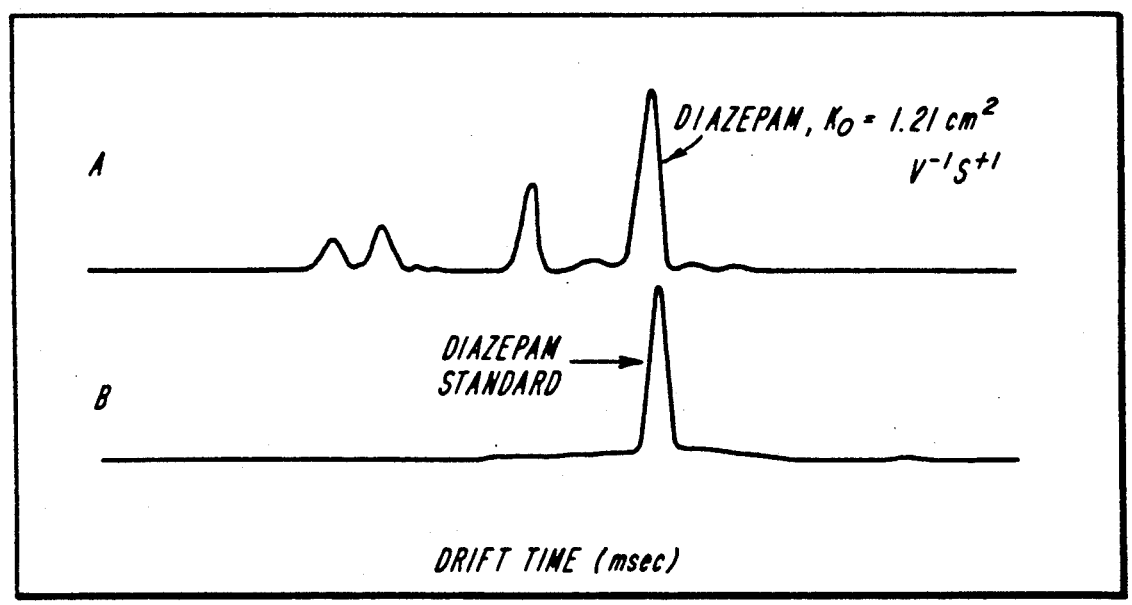
FIG. 2 is a tracing of an ion drift pattern obtained from a serum sample analyzed in an IMS.

A gas carrier stream is allowed to flow through the sampler-concentrator tube when it is placed into the heated inlet of the IMS (see FIG. 1). The compound-of-interest vaporizes immediately and is flushed with the carrier gas stream to the ion reaction chamber of the IMS where it is ionized. Positively and/or negatively charged ions, characteristic of the sample, are formed and are accelerated down the drift region to the collector which is at ground potential. Resolution of the ionic species is by way of their different mobilities through a drift gas while under the influence of the drift field. A plot of ion current versus drift time results in a positive or negative ion mobility spectrum depending on the polarity of the applied electric field. Accordingly, drift time (msec) or ion mobility reduced to standard temperature and pressure $K_0$, ($cm^2V^{-1}s^{-1}$), much as retention time in gas chromatography, is used as a qualitative measure of specific ions. The discriminatory power of the $K_0$ values and the specificity of the IMS have been reported in some detail in previous publications (See, e.g., Lawrence (1986) Anal. Chem. 58:1269-1272; Lawrence (1987) Forensic Sci. Intl. 34:73-83). Representative ion drift patterns are shown in FIG. 2, in which a serum sample containing diazepam has been analyzed.

The claimed subject matter can be further understood from the following non-limiting examples.

(1) Sampler-Concentrator Preparation

The sampler-concentrator device used consisted of Pyrex tubing (60 mm×3 mm) with a restriction in the middle, and containing, on one side of the restriction, about 30 mg of a first adsorbent, sodium-calcium hydrate, and on the other side of the restriction, about 30 mg of a second adsorbent, Tenax-GC (35-60 mesh; Akzo Research and Engineering N.V., Arnhem, Netherlands). The Tenax adsorbent was held in place with small plugs of silanized glass wool. The tubes were conditioned overnight at 250° C. in a helium stream at a flow rate of 50 $cm^3$/min. A chromatogram was recorded to check the purity of each tube before use. Neither peaks nor baseline drift were observed for tubes conditioned and then stored for up to 3 days. Air was drawn through the tubes by a diaphragm pump connected to a flow meter with ballast volume.

(2) IMS Calibration

Calibration of the (Phemto-Chem 100) IMS (PCP, Inc., West Palm Beach, FL) was achieved by injecting known amounts of pure benzodiazepine and determining the corresponding drift time or reduced mobility. The relative standard deviation of the $K_0$ values calculated from 10 replicate analyses was $\leq 0.1\%$. The experimental parameters used to operate the IMS are presented in TABLE 1.

TABLE 1

| Parameter | Value |
| --- | --- |
| drift length | 8 cm |
| drift voltage | +2700 V |
| carrier gas (purified air) | 200 mL/min |
| inlet and drift temperature | 220° C. |
| pressure | Atmosphere |
| dwell time | 20 μsec/channel |
| gate width | 0.2 msec[a] |
| delay time | 6 msec |

[a]Peaks were symmetrical with only 0.4 msec in width at 50% peak height.

Mass identification of ions giving particular mobility peaks was confirmed in a separate set of experiments by interfacing the IMS to a quadrupole mass spectrometer (PCP, Inc., West Palm Beach, FL).

3. Sampling

Blood and urine samples were obtained from the following groups of patients at a hospital:

(a) patients admitted to a hospital's Emergency Room with a history of benzodiazepine overdose. The approximate amount of drug and the interval between intake and admission was recorded whenever this information was available;

(b) in-patients at the hospital who were receiving therapeutic amounts of diazepam and oxazepam;

(c) patients admitted to the hospital with a non-benzodiazepine overdose; and (d) a control group of patients on no medications.

4. Separation and IMS Analysis

Serum was separated from blood cells by centrifugation. 2 μl of serum were transferred using a micropipette to the sampler-concentrator device, with the sample being deposited on the glass wool plug of the device. The device was heated to 100° C. for 10 seconds to desorb native constituents from the sodium-calcium hydrate. The desorbed material was vented without allowing it to proceed to the IMS. The device was then inserted into the heated inlet of the IMS.

The sampler-concentrator device was then heated to 150° C. to desorb the benzodiazepine from the sodium-calcium hydrate. Vaporized benzodiazepine was then vented to the Tenax mesh where it is retained. The tube was heated to 220° C. to desorb the benzodiazepine compound which was then transferred in vapor phase by the gas stream flow to the IMS.

Drug identification normally was achieved within 20 seconds. A representative IMS result from a serum sample is shown in FIG. 2. The diazepam peak in the sample (a) is identified by comparison with a diazepam standard (b).

5. Confirmation by GC-MS

50 μl of internal standard (15 mg/L prazepam) were added to 1.0 ml of serum sample. Concentrated ammonium hydroxide (0.2 ml) was added prior to extraction with 4.5 ml of n-butyl chloride. The samples were shaken for 5 minutes and then centrifuged. The organic layer was removed and evaporated. The sample was reconstituted in 25 μl ethanol; 2 μl were then injected into the gas chromatograph. Quantitation was done by comparison to standard curves obtained for diazepam and nordiazepam.

Gas chromatography was performed on a HP 5880A instrument (Hewlett Packard, Palo Alto, CA) with a nitrogen/phosphorus detector. A 15-M DB-1 fused silica capillary column was programmed from 120° C. to 295° C. increasing at 8° C. per minute. The helium flow was 2 ml/min. Mass spectra were obtained using 4500 Finnegan mass spectrometer (Cincinnati, Ohio) in the electron impact mode.

6. Confirmation by FPIA

100 μl samples of serum were analyzed by FPIA using a TDx Analyzer (Abbott Diagnostics, Inc., Abbott Park, IL). The analyzer was operated in accordance with the operator's manual, and the specific variables used for the assays were established by Abbott. The instrument was calibrated at the beginning of the evaluation with six calibrators (provided by Abbott).

7. Results

Eight patients were admitted with benzodiazepine overdose; the presence of the drug was confirmed in seven by the combination of GC-MS and FPIA (TABLE 2). In one patient, the presence of drug detected by IMS but not FPIA likely indicates the higher sensitivity of IMS (oxazepam is difficult to detect by GC-MS). Of these eight patients, three had other drugs detected by GC-MS; the presence of these drugs did not cause any false negatives by IMS. None of the patients taking therapeutic amounts of benzodiazepines (5–15 mg/day) had any detectable drug in serum by IMS. Benzodiazepines were not detected either by IMS or GC-MS in any of the 12 patients with non-benzodiazepine overdoses. The cut-off level at which benzodiazepines are detected by IMS was 2 μg/ml.

TABLE 2

| Sample No. | Drug(s) ingested | Drug(s) identified by: | | |
|---|---|---|---|---|
| | | IMS | FPIA | GC-MS |
| 1. | Diazepam | Diazepam | Benzodiazepines Acetominophen | Diazepam Acetominophen |
| 2. | Diazepam | Diazepam | Benzodiazepines | Diazepam |
| 3. | Oxazepam | Oxazepam | Oxazepam | * |
| 4. | Salicylates | — | Salicylates | — |
| 5. | Oxazepam | Oxazepam | Benzodiazepines | * |
| 6. | Tricyclic antidepressants | — | — | — |
| 7. | Acetominophen | — | — | — |
| 8. | Acetominophen | — | Acetominophen | Acetominophen |
| 9. | Diazepam | — | — | Diazepam |
| 10. | Diazepam | Diazepam | Benzodiazepines | Diazepam Acetominophen |
| 11. | Oxazepam | Oxazepam | Benzodiazepines | * |
| 12. | Diphenhydramine Carbamezepine | — — | — Carbamezepine | Diphenhydramine Carbamezepine |
| 13. | Diazepam Isopropanol | Diazepam | Benzodiazepines | Diazepam Isopropanol |
| 14. | Unknown drugs or drug mixtures (6 patients) | Cocaine | — | Cocaine |

* = Oxazepam decomposes with GS and is therefore difficult to detect using GC-MS.

In urine samples, the following drugs were identified by IMS and subsequently confirmed by FPIA and GC-MS: benzodiazepines (flurazepam, diazepam and oxazepam), cocaine, and amytryptyline. The level of detection was 2 μg/ml. In addition, the presence of various phospholipids were tested for in amniotic fluid and commercial amniotic fluid standard; phosphatidylcholine, phosphatidyl inositol, lecithin, and sphingomyelin were the species identified.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method of detecting a compound-of-interest in a body fluid comprising the steps of:
   (a) obtaining a sample of a body fluid in liquid phase, said fluid sample including a plurality of native constituents and a compound-of-interest;
   (b) separating said compound-of-interest from said native constituents in said body fluid sample; and
   (c) analyzing said fluid sample with an ion mobility spectrometer to determine the presence of said compound-of-interest therein.

2. The method of claim 1 wherein said obtaining step further comprises obtaining a sample of a body fluid in the liquid phase, said body fluid selected from the group consisting of blood, serum, saliva, urine, semen, amniotic fluid, cerebrospinal fluid, and lacrimal secretions.

3. The method of claim 1 wherein said separating step comprises:
   (a) adsorbing said fluid sample onto an adsorbent;
   (b) selectively removing said native constituents therefrom; and
   (c) liberating said compound-of-interest, said liberated compound-of-interest being delivered to said ion mobility spectrometer.

4. The method of claim 2 wherein:
said removing step comprises converting said adsorbed native constituents to the vapor phase, said vaporized native constituents desorbing from said adsorbent, and then venting said vaporized native constituents away from said adsorbent; and
said liberating step comprises changing said adsorbed compound-of-interest to the vapor phase, said vaporized compound-of-interest thereby desorbing from said adsorbent.

5. The method of claim 5 wherein:
said converting step comprises heating said adsorbent to a first temperature sufficient to convert said absorbed native constituents to the vapor phase, and
and wherein said changing step comprises heating said adsorbent to a second temperature sufficient to convert said adsorbed compound-of-interest to the vapor phase, said second temperature being higher than said first temperature.

6. The method of claim 3 wherein said separating step comprises:
   (a) adsorbing said fluid sample onto a first adsorbent;
   (b) removing said native constituents from said first adsorbent;
   (c) removing said compound-of-interest from said first adsorbent;
   (d) adsorbing said compound-of-interest onto a second adsorbent, said second adsorbent having an affinity for said compound-of-interest; and
   (e) liberating said compound-of-interest from said second absorbent, said liberated compound-of-interest being delivered to said ion mobility spectrometer.

7. The method of claim 6 wherein:
   (a) said removing step (b) comprises converting said adsorbed native constituents to the vapor phase;

(b) said removing step (c) comprises converting said adsorbed compound-of-interest to the vapor phase; and
(c) said liberating step comprises converting said absorbed compound-of-interest to the vapor phase.

8. The method of claim 7 wherein:

said first converting step (a) comprises heating said first adsorbent to a first temperature sufficient to desorb at least most of said absorbed native constituents in vapor phase therefrom;

said converting step (b) comprises heating said first adsorbent to a second temperature sufficient to desorb said adsorbed compound-of-interest in vapor phase therefrom, said second temperature being higher than said first temperature; and said converting step (c) comprises heating said second adsorbent to a third temperature sufficient to desorb said adsorbed compound-of-interest in vapor phase therefrom.

* * * * *

UNITED STATES PATENT AND TRADEMARK OFFICE
CERTIFICATE OF CORRECTION

PATENT NO. : 4,988,628

DATED : January 29, 1991

INVENTOR(S) : Amin A. Nanji and André H. Lawrence

It is certified that error appears in the above-identified patent and that said Letters Patent is hereby corrected as shown below:

On the title page, under item [19], replace "Nanji" with --Nanji et al.--; and in item [75], please delete "Inventor: Amin A. Nanji, Wellesley, Mass." and insert --Inventors: Amin A. Nanji, Wellesley, Mass. and Andre H. Lawrence, Gloucester, Ontario, Canada--.

Column 8, line 8, please replace "claim 2" with --claim 3--.

Column 8, line 42, please replace "claim 5" with --claim 4--.

Column 8, line 52, please replace "claim 3" with --claim 1--.

Signed and Sealed this

Eighth Day of December, 1992

*Attest:*

DOUGLAS B. COMER

*Attesting Officer*   *Acting Commissioner of Patents and Trademarks*